(12) United States Patent
Kang et al.

(10) Patent No.: US 10,330,576 B2
(45) Date of Patent: Jun. 25, 2019

(54) SENSOR FOR MEASURING SHEAR FORCE AND DUMMY FOR MEASURING SHEAR FORCE USING THE SAME

(71) Applicants: Hyundai Motor Company, Seoul (KR); Kia Motors Corporation, Seoul (KR); University Industry Foundation, Yonsei University Wonju Campus, Wonju-si (KR)

(72) Inventors: Tae Uk Kang, Seoul (KR); Han Sung Kim, Wonju-si (KR); Seong Guk Kim, Wonju-si (KR); Dong Hyun Kim, Yongin-si (KR); Dong Hyun Hwang, Wonju-si (KR); Han A. Lee, Wonju-si (KR); Ye Eun Song, Wonju-si (KR)

(73) Assignees: Hyundai Motor Company, Seoul (KR); Kia Motors Corporation, Seoul (KR); University Industry Foundation, Yonsei University Wonju Campus, Wonju-si (KR)

( * ) Notice: Subject to any disclaimer, the term of this patent is extended or adjusted under 35 U.S.C. 154(b) by 0 days.

(21) Appl. No.: 15/690,761

(22) Filed: Aug. 30, 2017

(65) Prior Publication Data
US 2018/0164198 A1 Jun. 14, 2018

(30) Foreign Application Priority Data
Dec. 13, 2016 (KR) .......................... 10-2016-0169975

(51) Int. Cl.
*G01N 3/24* (2006.01)
*G01M 17/007* (2006.01)
(Continued)

(52) U.S. Cl.
CPC .............. *G01N 3/24* (2013.01); *G01L 5/0052* (2013.01); *G01M 17/0078* (2013.01); *G09B 23/06* (2013.01); *B60N 2002/0268* (2013.01)

(58) Field of Classification Search
CPC .... G01N 3/24; G01L 1/22; G01L 5/00; G01L 5/0052; G01M 17/00; G01M 17/0078; B60N 2002/0268; G09B 23/06
(Continued)

(56) References Cited

U.S. PATENT DOCUMENTS 5,526,208 A * 6/1996 Hatch .................. G11B 5/4846
360/245.8
9,352,456 B2 * 5/2016 Murthy .................. B25B 21/00
(Continued)

FOREIGN PATENT DOCUMENTS

JP 2011-209285 A 10/2011
JP 5119293 B2 1/2013
(Continued)

*Primary Examiner* — Max H Noori
(74) *Attorney, Agent, or Firm* — Morgan, Lewis & Bockius LLP (57) ABSTRACT

A sensor for measuring shear force and a dummy for testing a vehicle using the same are provided herein. A sensor for measuring shear force which is configured to quantitatively accurately measure shear force applied to a human body who sits on a vehicle seat, and a dummy for measuring shear force using the sensor are provided, wherein the sensor for measuring shear force includes an upper block, an intermediate block and a lower block and is configured such that a first strain gauge is mounted upright between the upper block and the intermediate block and a second strain gauge is mounted upright between the intermediate block and the lower block so that the shear force can be accurately measured without being affected by horizontal tensile force.

13 Claims, 9 Drawing Sheets

(51) Int. Cl.
  *G01L 5/00* (2006.01)
  *G09B 23/06* (2006.01)
  *B60N 2/02* (2006.01)

(58) Field of Classification Search
  USPC .......................................................... 73/841
  See application file for complete search history.

(56) References Cited

U.S. PATENT DOCUMENTS

| | | | |
|---|---|---|---|
| 2003/0042688 A1* | 3/2003 | Davie .................... | F16J 15/061 |
| | | | 277/590 |
| 2003/0218432 A1* | 11/2003 | Song .................... | G09G 3/2944 |
| | | | 315/169.1 |
| 2004/0099852 A1* | 5/2004 | Hoffend, Jr. ............ | A63J 1/028 |
| | | | 254/331 |
| 2004/0187593 A1* | 9/2004 | Okada .................... | G01L 5/165 |
| | | | 73/780 |
| 2006/0021453 A1* | 2/2006 | Kutlu .................... | G01L 5/0047 |
| | | | 73/862.474 |
| 2008/0167663 A1* | 7/2008 | De Mathelin ...... | A61B 17/3403 |
| | | | 606/130 |
| 2015/0128725 A1* | 5/2015 | Ichige .................. | G01L 1/2231 |
| | | | 73/862.045 |
| 2015/0219179 A1* | 8/2015 | Cui ........................ | F16F 15/03 |
| | | | 248/550 |

FOREIGN PATENT DOCUMENTS

| | | |
|---|---|---|
| KR | 10-1008845 B1 | 1/2011 |
| KR | 10-1262554 B1 | 5/2013 |
| KR | 10-1361210 B1 | 2/2014 |

* cited by examiner

250
SENSOR FOR MEASURING SHEAR FORCE AND DUMMY FOR MEASURING SHEAR FORCE USING THE SAME

CROSS-REFERENCE(S) TO RELATED APPLICATIONS

The present application claims priority to Korean Patent Application No. 10-2016-0169975 filed on Dec. 13, 2016, the entire contents of which are incorporated herein for all purposes by this reference.

BACKGROUND OF THE INVENTION

Field of the Invention

The present invention relates to a sensor for measuring shear force and a dummy for testing a vehicle using the same. More particularly, it relates to a sensor for measuring shear force which is configured to quantitatively accurately measure shear force applied to a human body who sits on a vehicle seat, and a dummy for measuring shear force using the sensor.

Description of Related Art

Seats for vehicles are typically designed to have a structure configured to primarily protect an occupant from vibrations or shocks in light of characteristic values of the human body, and are manufactured to have a structure capable of providing riding comfort.

Particularly, depending on the structure of the seat for vehicles, muscle fatigue of the occupant and the load applied to the lumbar of the occupant vary. Therefore, to accomplish a high level of comfort while riding in the seat, when the seat is designed, the muscle fatigue and the load applied to the lumbar of the occupant should be sufficiently considered.

Therefore, to development the seat, a process of measuring the pressure distribution on the occupant who sits on the seat is required.

In the present regard, the process of measuring the pressure distribution on the occupant includes determining the vertical load caused by the vertebral body of the occupant. Furthermore, since the riding comfort of the seat is affected not only by the vertical load of the occupant but also by shear force generated when the occupant is on the seat, it is preferable that the shear force applied to the occupant as well as the vertical load caused by the occupant be determined.

Given the present case, a shear force measurement apparatus is provided by the present invention. In the present shear force measurement apparatus, a plurality of shear force sensors are disposed in a seat to accurately measure the shear forces applied to respective portions of the seat when an occupant sits on the seat. Thus, taking into account both the vertical load and the horizontal shear force that influence the spine's degree of discomfort or muscle fatigue when an occupant sits on the seat, the shear force measurement apparatus can quantitatively measure the spine's discomfort degree and muscle fatigue.

However, in a conventional shear force measurement sensor, longitudinal and lateral strain gauges are disposed in the horizontal direction. Therefore, the resolution of the strain gauges is limited by the slight variation in the shearing load measured by each gauge.

Furthermore, in the conventional shear force measurement sensor, to minimize the effects of a vertical tensile force on the strain gauge that is horizontally disposed between plates forming the sensor, a separate ball bearing is provided. However, the vertical tensile force still has an effect on the strain gauge, thus reducing the accuracy in measuring the shear force.

The information disclosed in this Background of the Invention section is only for enhancement of understanding of the background of the invention and should not be taken as an acknowledgement or any form of suggestion that this information forms the prior art already known to a person skilled in the art.

BRIEF SUMMARY

The present invention is directed to provide a sensor for measuring shear force and a dummy for testing a vehicle using the same, the sensor including an upper block, an intermediate block and a lower block. The sensor is configured, wherein a first strain gauge is mounted upright between the upper block and the intermediate block, and a second strain gauge is mounted upright between the intermediate block and the lower block so that the shear force can be accurately measured without being affected by a horizontal tensile force.

One aspect of the present invention is directed to providing a sensor for measuring a shear force. The sensor includes an upper block including an upper horizontal plate; an intermediate block including an intermediate horizontal plate; and a lower block including a lower horizontal plate, wherein the upper block, the intermediate block and the lower block are assembled to be separated apart from one another by column structures; a first strain gauge is placed upright between the upper block and the intermediate block with being oriented in an X-axis direction; and a second strain gauge is placed upright between the intermediate block and the lower block with being oriented in a Y-axis direction.

In an exemplary embodiment, an upper column may be integrally formed on a lower surface of the upper horizontal plate and be brought into close contact with an upper surface of the intermediate horizontal plate, and a first intermediate column may be integrally formed on the upper surface of the intermediate horizontal plate and be brought into close contact with the lower surface of the upper horizontal plate.

In another exemplary embodiment, a second intermediate column may be formed on a lower surface of the intermediate horizontal plate and be brought into close contact with an upper surface of the lower horizontal plate, and a first lower column and a second lower column may be integrally formed on the upper surface of the lower plate and be brought into close contact with a lower surface of the intermediate horizontal plate.

In still another exemplary embodiment, a first end of the first strain gauge may be brought into close contact with and assembled with a front surface of the upper column of the upper block, and a second end of the first strain gauge may be brought into close contact with and assembled with a rear surface of the first intermediate column of the intermediate block.

In yet another exemplary embodiment, the upper column and the first intermediate column may have the same height as each other, and a height of the first strain gauge may be less than the height of the upper column and the first intermediate column.

In still yet another exemplary embodiment, a first end of the second strain gauge may be brought into close contact with and assembled with a right side surface of the second intermediate column of the intermediate block, and a second end of the second strain gauge may be brought into close contact with and assembled with a left side surface of the first lower column of the lower block.

The second intermediate column, the first lower column and the second lower column may have the same height as one another, and a height of the second strain gauge may be less than the height of the second intermediate column, the first lower column and the second lower column.

In a further exemplary embodiment, a signal line wiring hole may be formed in the intermediate horizontal plate of the intermediate block so that a signal line of the second strain gauge passes through the signal line wiring hole.

In another further exemplary embodiment, a circular support plate may be attached on an upper surface of the upper block, and a circular silicon contact plate may be attached on the circular support plate.

The other aspect of the present invention is directed to providing a dummy for measuring a shear force, including: an upper body dummy and a lower body dummy to each of which the sensor having the above-mentioned configuration is separably mounted; and a hinge connector connecting the upper body dummy to the lower body dummy using a hinge.

In an exemplary embodiment, each of the upper body dummy and the lower body dummy may include a plurality of insertion holes, into each of which the sensor for measuring shear force is inserted and fixed, and each of which is formed in a concave shape in a portion thereof making contact with a surface of a vehicle seat. A signal line lead-out hole may be formed in a portion of an inner wall of each of the insertion holes so that a signal line of the sensor for measuring the shear force is drawn out through the signal line lead-out hole.

In another exemplary embodiment, seventeen or more insertion holes may be formed in the upper body dummy at positions corresponding to a spine line thereof, opposite sides of the spine line, and portions thereof making contact with side bolsters of a seatback, and fifteen or more insertion holes may be formed in the lower body dummy at positions corresponding to a hip portion thereof, both thigh lines, and portions thereof making contact with side bolsters of a seat cushion.

Other aspects and exemplary embodiments of the invention are discussed infra.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g. fuels derived from resources other than petroleum). As referred to herein, a hybrid vehicle is a vehicle that has two or more sources of power, for example both gasoline-powered and electric-powered vehicles.

The above and other features of the invention are discussed infra.

The methods and apparatuses of the present invention have other features and advantages which will be apparent from or are set forth in more detail in the accompanying drawings, which are incorporated herein, and the following Detailed Description, which together server to explain certain principles of the present invention.

It should be understood that the appended drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Reference will now be made in detail to various embodiments of the present invention(s), examples of which are illustrated in the accompanying drawings and described below. While the invention(s) will be described in conjunction with exemplary embodiments, it will be understood that present description is not intended to limit the invention(s) to those exemplary embodiments. On the contrary, the invention(s) is/are intended to cover not only the exemplary embodiments, but also various alternatives, modifications, equivalents and other embodiments, which may be included within the spirit and scope of the invention as defined by the appended claims.

Hereinafter, an exemplary embodiment of the present invention will be described in detail with reference to the accompanying drawings.

FIGS. 1 to 8 illustrate a sensor for measuring shear force according to an exemplary embodiment of the present invention.

As shown in FIG. 1 to FIG. 8, the shear force measurement sensor 100 according to an exemplary embodiment of the present invention may include three blocks which include an upper block 110, an intermediate block 130 and a lower block 150; and two strain gauges which include a first strain gauge 120 placed upright between the upper block 110 and the intermediate block 130, and a second strain gauge 140 placed upright between the intermediate block 130 and the lower block 150.

Figure 1:
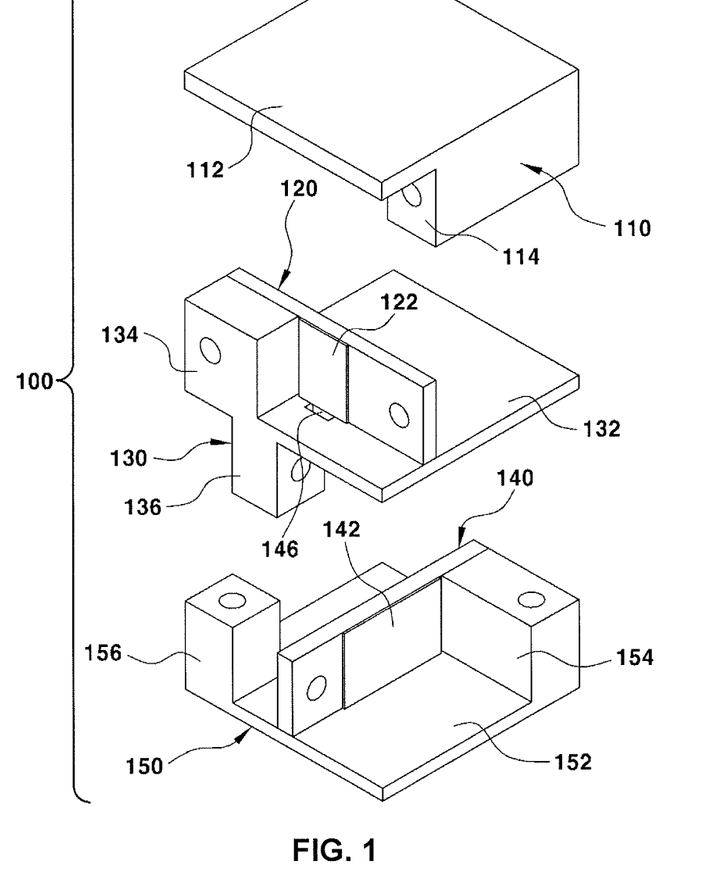
FIG. 1 is an exploded perspective view illustrating a sensor for measuring shear force according to an exemplary embodiment of the present invention.
Figure 2:
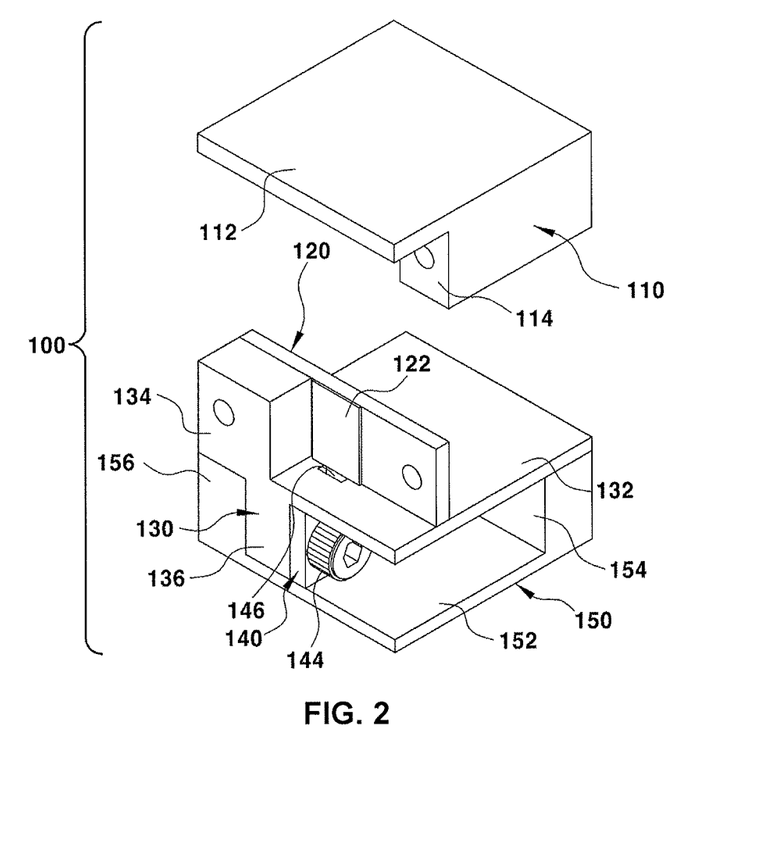
FIG. 2 is a perspective view illustrating the shear force measurement sensor from which an upper block is separated, according to an exemplary embodiment of the present invention.
Figure 3:
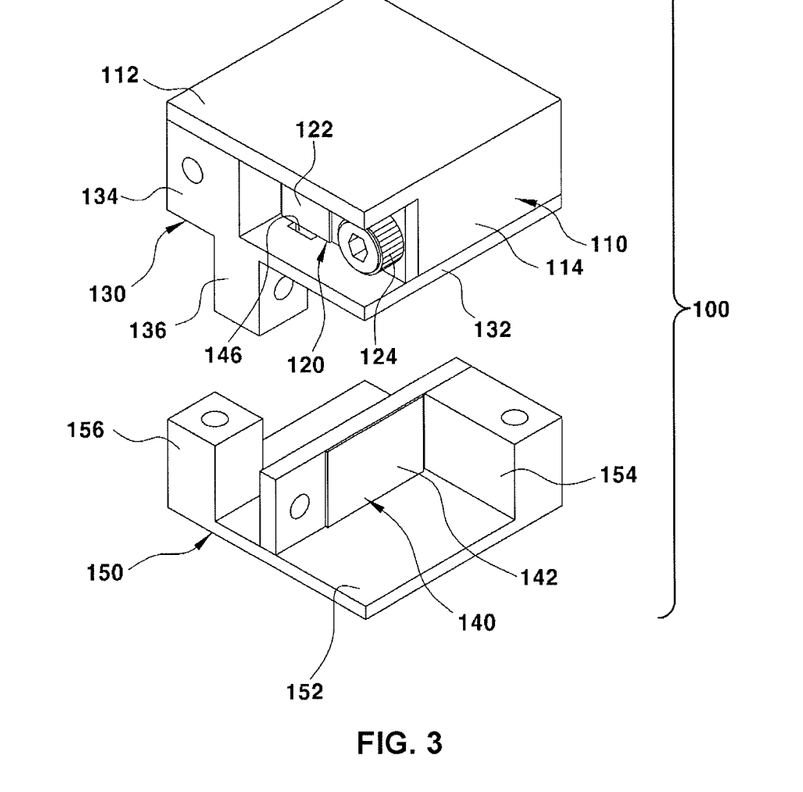
FIG. 3 is a perspective view illustrating the shear force measurement sensor from which a lower block is separated, according to an exemplary embodiment of the present invention.

The upper block 110 includes an upper horizontal plate 112 having a rectangular planar shape, and an upper column 114 which integrally protrudes from a lower surface of the upper horizontal plate 112.

The upper column 114 has a rectangular block shape extending from a corner of the upper horizontal plate 112 to a predetermined position of each of both sides of the corner.

The intermediate block 130 includes an intermediate horizontal plate 132 having a rectangular planar shape, a first intermediate column 134 which integrally protrudes from an upper surface of the intermediate horizontal plate 132 and comes into close contact with the lower surface of the upper horizontal plate 112 of the upper block 110, and a second intermediate column 136 which integrally protrudes from a lower surface of the intermediate horizontal plate 132.

The first intermediate column 134 is disposed at a position at which it does not make contact with the upper column 114, preferably, on a corner of the intermediate horizontal plate 132 that is diagonally opposite to the upper column 114. The second intermediate column 136 is disposed on the lower surface of the intermediate horizontal surface 132 at an inside position separated apart from the position at which the first intermediate column 134 is disposed.

The lower block 150 includes a lower horizontal plate 152 having a rectangular planar shape, a first lower column 154 which integrally protrudes from a corner of an upper surface of the lower horizontal plate 152 (a corner that corresponds to the corner on which the upper column of the upper block is disposed) and makes close contact with the lower surface of the intermediate horizontal plate 132 of the intermediate block 130, and a second lower column 156 which integrally protrudes from a corner of the upper surface of the lower horizontal plate 152 that is diagonally opposite to the first lower column 154 and makes close contact with the lower surface of the intermediate horizontal plate 132.

Sensor chips 122 and 142 are respectively attached to first surfaces of middle portions of the first and second strain gauges 120 and 140 respectively. Each of the first and second strain gauges 120 and 140 has a long rectangular planar structure that has, on opposite ends thereof, assembly holes for screw coupling.

The first strain gauge 120 is placed upright between the upper block 110 and the intermediate block 130 and oriented in an X-axis direction. A first end of the first strain gauge 120 is brought into close contact with a front surface of the upper column 114 and assembled therewith by a screw 124. A second end of the first strain gauge 120 is brought into close contact with a rear surface of the first intermediate column 134 and assembled therewith by a screw 124.

The second strain gauge 140 is placed upright between the intermediate block 130 and the lower block 150 and oriented in a Y-axis direction. A first end of the second strain gauge 140 is brought into close contact with a right side surface of the second intermediate column 136 and assembled therewith by a screw 144. A second end of the second strain gauge 140 is brought into close contact with a left side surface of the first lower column 154 and assembled therewith by a screw 144.

Hereinbelow, a process of assembling the shear force measurement sensor according to an exemplary embodiment of the present invention will be described in more detail.

The upper block 110 and the intermediate block 130 are stacked vertically, wherein the first end of the first strain gauge 120 is brought into close contact with the front surface of the upper column 114 while the second end thereof is brought into close contact with the rear surface of the first intermediate column 134.

Thereafter, the first end of the first strain gauge 120 is assembled with the front surface of the upper column 114 by the screw 124. The second end of the first strain gauge 120 is assembled with the rear surface of the first intermediate column 134 by the screw 124. Thus, the first strain gauge 120 is placed upright between the upper block 110 and the intermediate block 130 and oriented in the X-axis direction.

In the present regard, a lower surface of the upper column 114 comes into contact with the upper surface of the intermediate horizontal plate 132 of the intermediate block 130. An upper surface of the first intermediate column 134 comes into contact with the lower surface of the upper horizontal plate 112 of the upper block 110.

The intermediate block 130 and the lower block 150 are stacked vertically, wherein the first end of the second strain gauge 140 comes into close contact with the right side surface of the second intermediate column 136 while the second end thereof comes into close contact with the left side surface of the first lower column 154.

Thereafter, the first end of the second strain gauge 140 is assembled with the right side surface of the second intermediate column 136 by the screw 144. The second end of the second strain gauge 140 is assembled with the left side surface of the first lower column 154 by the screw 144. Accordingly, the second strain gauge 140 is placed upright between the intermediate block 130 and the lower block 150 and oriented in the Y-axis direction.

In the present regard, a lower surface of the second intermediate column 136 comes into close contact with the upper surface of the lower horizontal plate 152 of the lower block 150. Upper surfaces of the first and second lower columns 154 and 156 respectively of the lower block 150 come into close contact with the lower surface of the intermediate horizontal plate 132 of the intermediate block 130.

Figure 9:
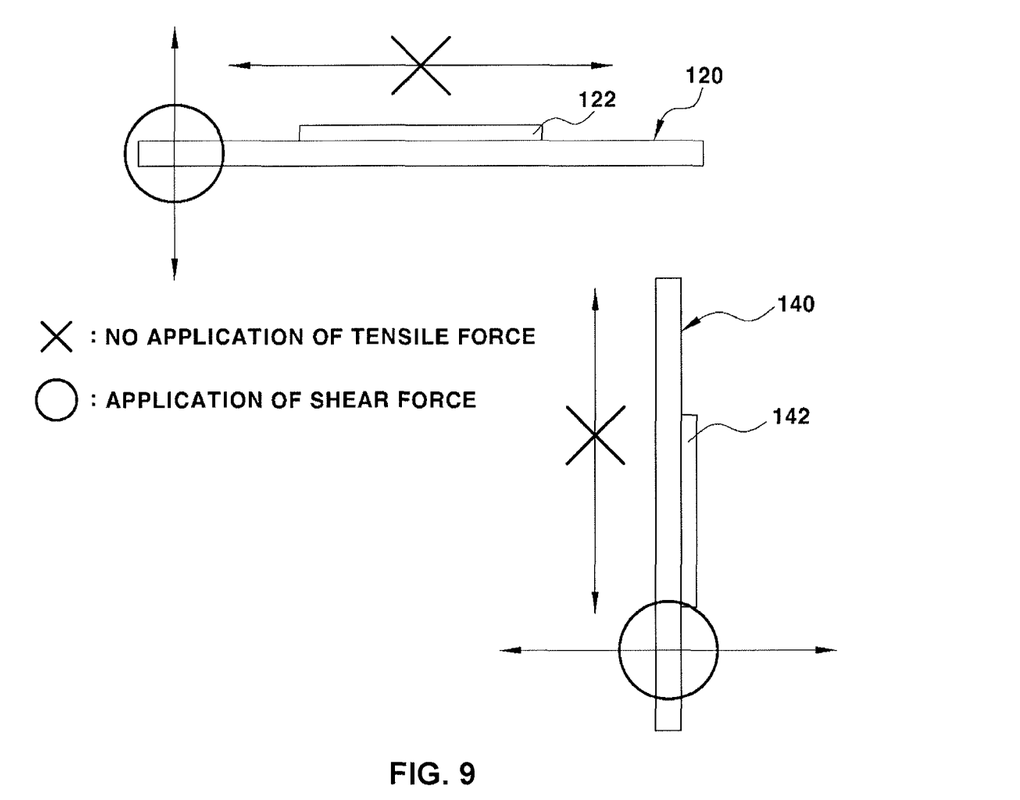
FIG. 9 is a schematic view illustrating directions in which shear force and tensile force are applied to the first and second strain gauges of the shear force measurement sensor according to an exemplary embodiment of the present invention.

The upper column 114 and the first intermediate column 134 have the same height as each other, and the height of the first strain gauge 120 is less than the height of the upper column 114 and the first intermediate column 134. Thereby, as shown in FIG. 9, the effects of the up and down tensile force and the left and right tensile force that are parallel with the plane of the first strain gauge 120 can be minimized. Consequently, only shear force perpendicular to the plane of the first strain gauge 120 can be efficiently and accurately measured by the first strain gauge 120.

For example, even when a tensile load or compressive load is applied to the upper block 110 and, simultaneously, the load is transmitted to the intermediate block 130 and the lower block 150 that are stacked and make contact with each other, the up-down tensile force and the left-right tensile force is not applied to the first strain gauge 120 because the height of the first strain gauge 120 is less than the height of the upper column 114 and the first intermediate column 134.

Consequently, the first stain gauge 120 can accurately measure only shear force perpendicular to the plane of the first strain gauge 120.

Likewise, the first lower column 154, the second lower column 156, and the second intermediate column 136 have the same height as one another. The height of the second strain gauge 140 is less than the first lower column 154, the second lower column 156 and the second intermediate column 136. Thus, as shown in FIG. 9, the effects of the up and down tensile force and the left and right tensile force that are parallel with the plane of the second strain gauge 140 can be minimized. Consequently, only shear force perpendicular to the plane of the second strain gauge 140 can be efficiently and accurately measured by the second strain gauge 140.

For example, even when a tensile load or compressive load is applied to the upper block 110 and, simultaneously, the load is transmitted to the intermediate block 130 and lower block 150 that are stacked and make contact with each other, the up-down tensile force or the left-right tensile force is not applied to the second strain gauge 140 because height of the second strain gauge 140 is less than the height of the second intermediate column 136, the first lower column 154 and the second lower column 156.
the second stain gauge 140 can accurately measure only shear force perpendicular to the plane of the second strain gauge 140.

A signal line wiring hole 146 is formed in the intermediate horizontal plate 132 of the intermediate block 130 so that a signal line extending from the sensor chip 142 of the second strain gauge 140 passes through the signal line wiring hole 146. The signal line of the sensor chip 142 can be drawn out above the intermediate block 130 through the signal line wiring hole 146 and then combined with a signal line extending from the sensor chip 122 of the first strain gauge 120 to be drawn out of a predetermined portion the upper block 110. In the present way, the signal lines of the sensor chips 122 and 142 can be easily connected to a controller.

Figure 4:
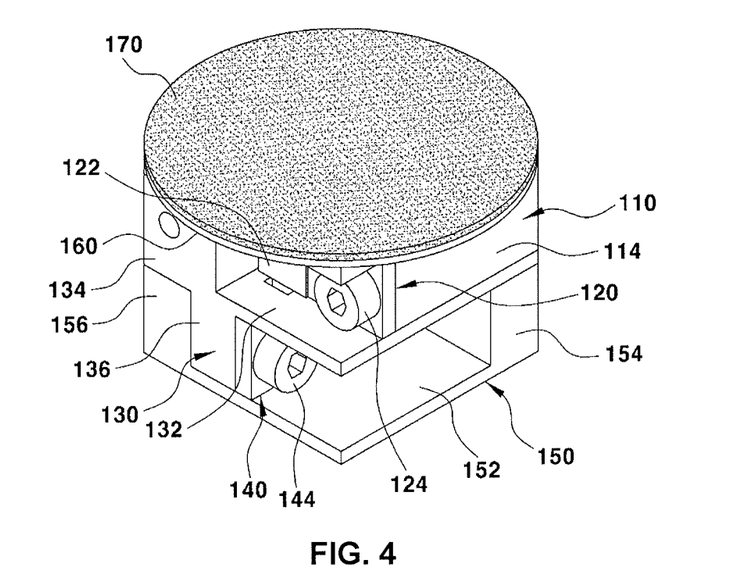
FIG. 4 and FIG. 5 are perspective views illustrating the assembled shear force measurement sensor according to an exemplary embodiment of the present invention.
Figure 5:
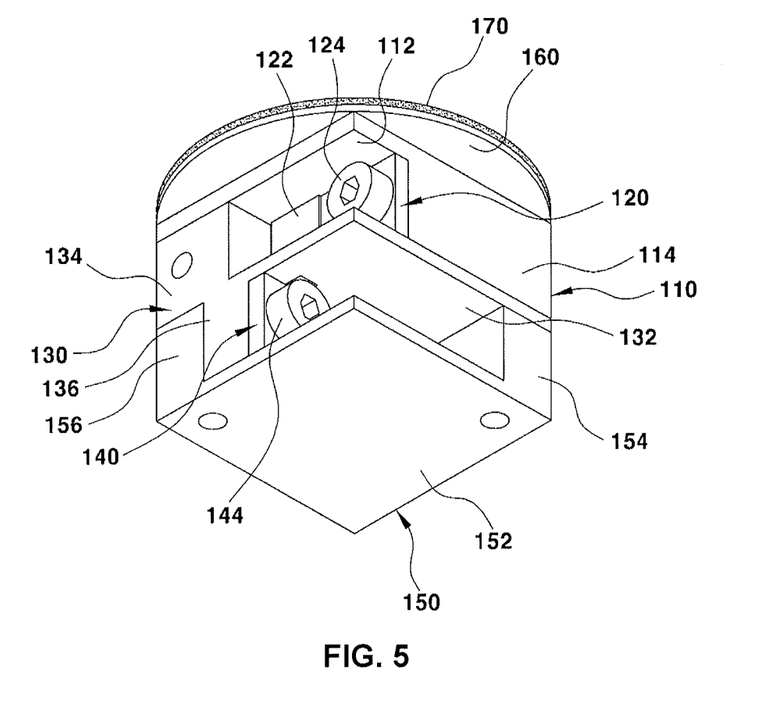
Figure 6:
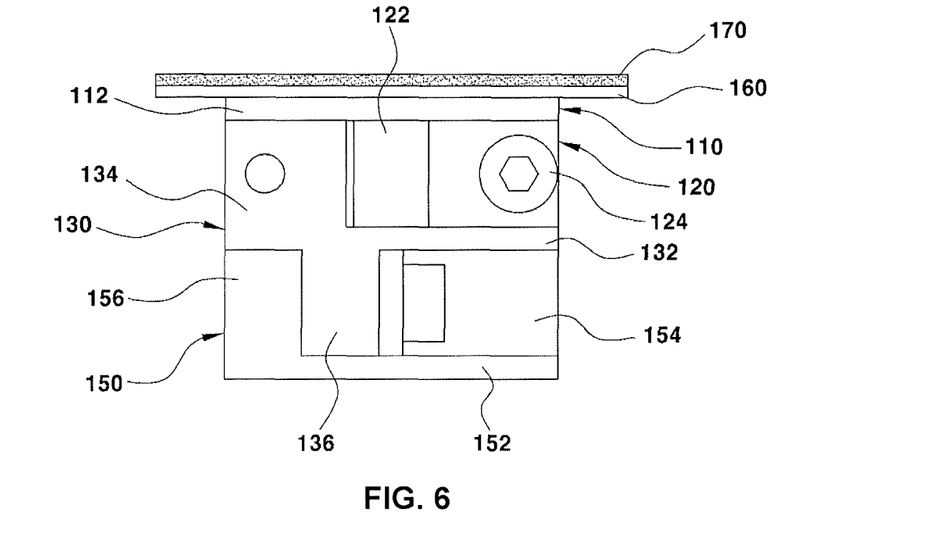
FIG. 6 is a front view illustrating the shear force measurement sensor according to an exemplary embodiment of the present invention.
Figure 7:
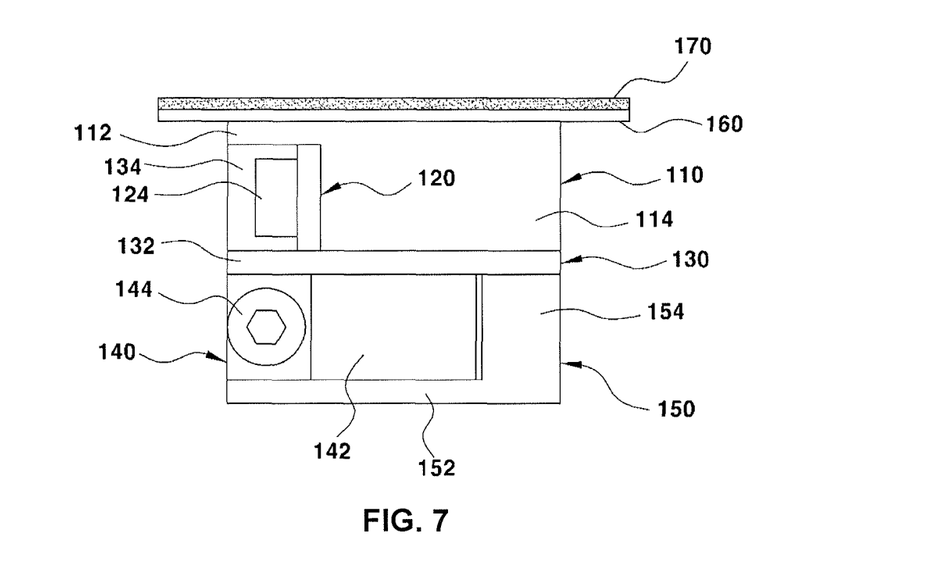
FIG. 7 is a side view illustrating the shear force measurement sensor according to an exemplary embodiment of the present invention.
Figure 8:
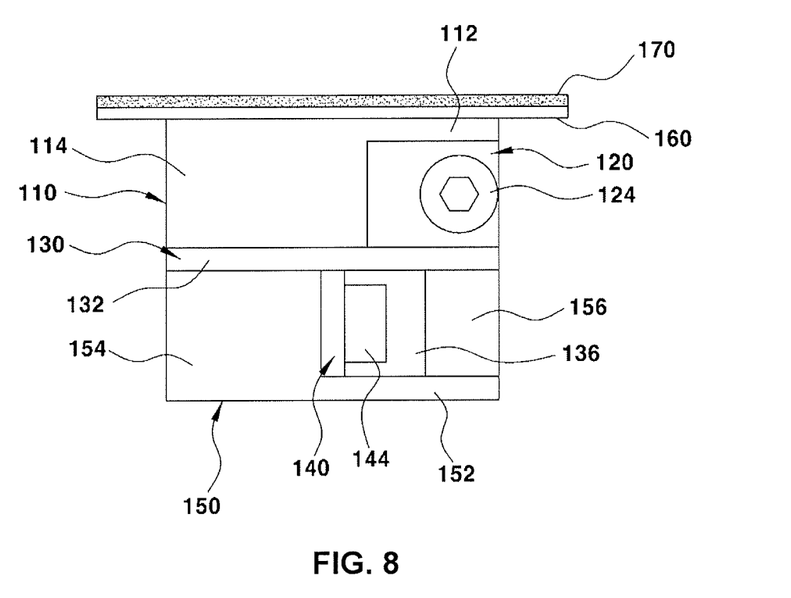
FIG. 8 is a rear view illustrating the shear force measurement sensor according to an exemplary embodiment of the present invention.

As shown in FIG. 4 and FIG. 5, the shear force measurement sensor 100 according to an exemplary embodiment of the present invention further includes a circular support plate 160 and a circular silicon contact plate 170 which are successively stacked on the upper block 110.

The reason why the circular support plate 160 and the circular silicon contact plate 170 are mounted on the upper surface of the upper block 110 is that since each block of the shear force measurement sensor has a cuboid shape, torsion may be caused on a corner portion of each block by a load and thus accuracy in measurement of shear force may be reduced.

Figure 10:
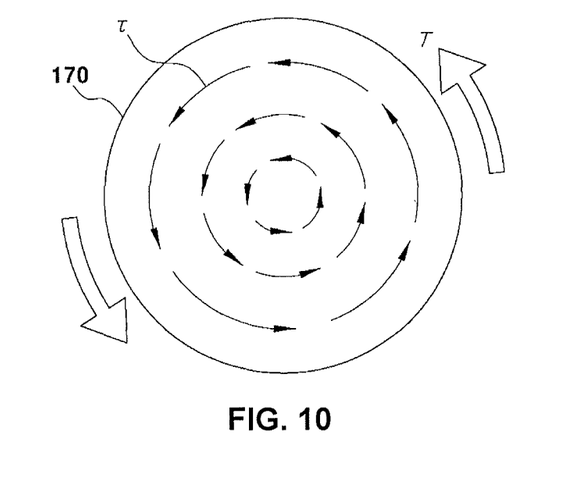
FIG. 10 is a schematic view illustrating application of force to a silicon contact plate of the shear force measurement sensor according to an exemplary embodiment of the present invention.

Given the present, the circular support plate 160 and the circular silicon contact plate 170 are mounted on the upper surface of the upper block 110. Thus, as shown in FIG. 10, uniform force can be applied to the strain gauge at any position, whereby the accuracy of the shear force measurement can be promoted.

Here, the circular silicon contact plate 170 is an element which makes contact a substantial target (e.g., a surface of a seat for vehicles) to be measured in shear force. circular silicon contact plate 170 functions to prevent the shear force measurement sensor from slipping from the target to be measured, thus contributing to increasing the accuracy the shear force measurement.

Hereinafter, a dummy for measuring shear force, to which the shear force measurement sensor of the present invention having the above-mentioned configuration is removably mounted, will be described.

Figure 11:
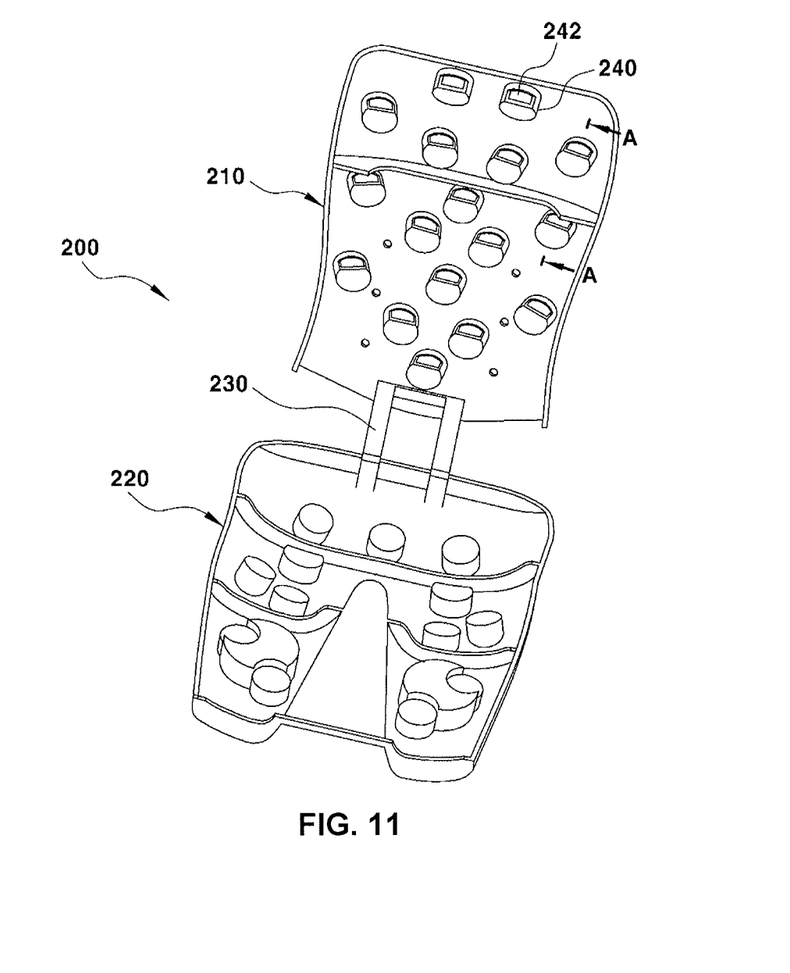
FIG. 11 is a perspective view illustrating a dummy for measuring shear force according to an exemplary embodiment the present invention.
Figure 12:
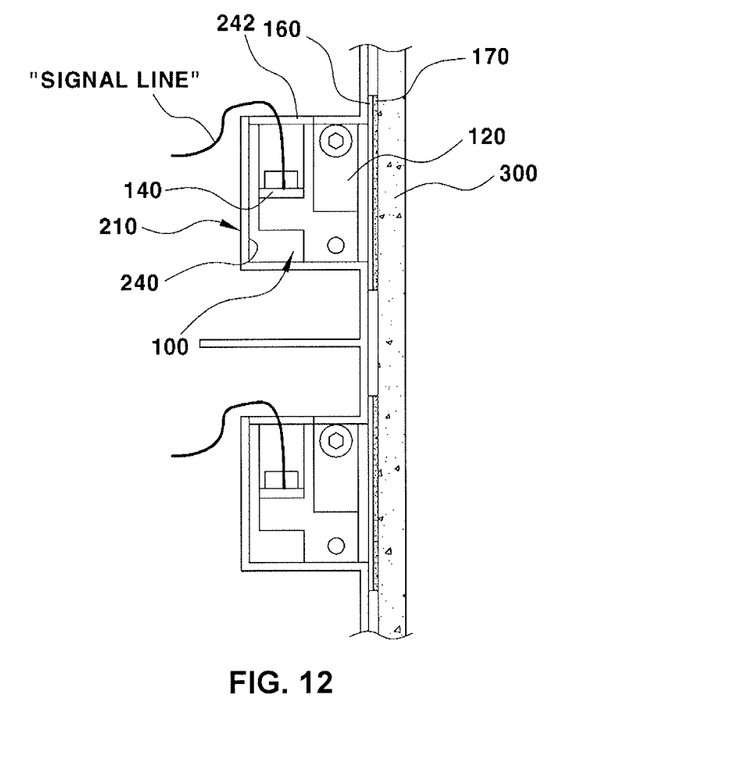
FIG. 12 illustrates the dummy for measuring shear force to which the shear force measurement sensor is mounted according to an exemplary embodiment of the present invention, and is a partial enlarged sectional view taken along link A-A of FIG. 11.

FIG. 11 is a perspective view illustrating the dummy for measuring the shear force according to an exemplary embodiment of the present invention. FIG. 12 is a partial enlarged sectional view illustrating the shear force measurement sensor disposed on the shear force measurement dummy according to an exemplary embodiment of the present invention.

As shown in FIG. 11, the shear force measurement dummy 200 is a dummy for simulating a state in which an occupant sits on a vehicle seat. The dummy includes an upper body dummy 210, a lower body dummy 220, and a hinge connector 230 which couples the upper body dummy 210 with the lower body dummy 220 using a hinge.

Furthermore, each of the upper body dummy 210 and the lower body dummy 220 includes a plurality of insertion holes 240, into each of which the shear force measurement sensor 100 is inserted and fixed, and each of which is formed in a concave shape in a portion thereof making contact with the surface of the vehicle seat. A signal line lead-out hole 242 through which the signal line of the shear force measurement sensor 100 is drawn out is formed in a portion of an inner wall of each insertion holes 240.

Preferably, seventeen or more insertion holes 240 are formed in the upper body dummy 210, and fifteen or more insertion holes 240 are formed in the lower body dummy 220. Thus, thirty-two or more shear force measurement sensors 100 may be disposed in the respective insertion holes 240.

In more detail, seventeen or more insertion holes 240 are formed in the upper dummy 210 at positions corresponding to the spine line of the occupant, opposite sides of the spine line, and portions making contact with side bolsters of a seatback (that protrude from opposite sides of the seatback to support the waist of the occupant). Fifteen or more insertion holes 240 are formed in the lower body dummy 220 at positions corresponding to the hip, both thigh lines, and portions making contact with side bolsters of a seat cushion.

As shown in FIG. 12, when thirty-two or more shear force measurement sensors 100 are disposed in the respective insertion holes 240, only the silicon contact plate 170 of each shear force measurement sensor 100 protrudes from the corresponding insertion hole 240 and is brought into contact with the surface of the vehicle seat 300 that is a substantial target to be measured in shear force. In the present way, the dummy simulates the state in which the occupant sits on the seat.

As such, the shear force measurement sensors 100 are disposed in the shear force measurement dummy 200 according to an exemplary embodiment of the present invention. When vibrations or the like are applied to the shear force measurement sensors 100 through the seat or the like while the vehicle travels, the shear force measurement sensors 100 can practically simulate and accurately measure the sear force to be applied to the occupant who sits on the seat.

As described above, the present invention has the following effects.

First, a first strain gauge is placed upright between an upper block and an intermediate block and oriented in an X-axis direction. A second strain gauge is placed upright between an intermediate block and a lower block and oriented in a Y-direction. Thereby, each strain gauge is seldom affected by left-right tensile force with respect to a direction parallel with the strain gauge. Consequently, only shear force perpendicular to the strain gauge can be efficiently and accurately measured by the strain gauge.

Second, the height of the first strain gauge is less than the height between the upper block and the intermediate block, and the height of the second strain gauge is less than the height between the intermediate block and the lower block. Thus, the vertical tensile force parallel with the strain gauge can be minimized, whereby only the shear force perpendicular to the strain gauge can be efficiently and accurately measured.

Third, a circular support plate and a circular silicon contact plate are stacked and attached to the upper block so that torsion is prevented from being applied to corners of block, and uniform force is applied to the sensor in all directions. Consequently, the force can be accurately measured.

Fourth, in the case where a dummy with a plurality of shear force measurement sensors is mounted on a vehicle seat, the dummy can directly simulate and accurately measure shear force to be applied to an occupant who sits on the seat.

For convenience in explanation and accurate definition in the appended claims, the terms "upper", "lower", "inner", "outer", "up", "down", "upwards", "downwards", "front", "rear", "back", "inside", "outside", "inwardly", "outwardly", "interior", "exterior", "forwards" and "backwards" are used to describe features of the exemplary embodiments with reference to the positions of such features as displayed in the figures.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled the art to make and utilize various exemplary embodiments of the present invention, as as various alternatives and modifications thereof. It is intended that the scope of the invention be defined by the Claims appended hereto and their equivalents.

What is claimed is:

1. A sensor for measuring a shear force, comprising:
an upper block including an upper horizontal plate, an intermediate block including an intermediate horizontal plate, and a lower block including a lower horizontal plate, wherein the upper block, the intermediate block and the lower block are stacked vertically and assembled to be separated apart from one another by column structures;
a first strain gauge placed upright with respect to the upper horizontal plate of the upper block and the intermediate horizontal plate of the intermediate block between the upper horizontal plate of the upper block and the intermediate horizontal plate of the intermediate block and oriented in an X-axis direction; and
a second strain gauge placed upright with respect to the intermediate horizontal plate and the lower horizontal plate between the intermediate horizontal plate of the intermediate block and the lower horizontal plate of the lower block and oriented in a Y-axis direction.

2. The sensor according to claim 1, wherein an upper column is integrally formed on a lower surface of the upper horizontal plate and is brought into contact with an upper surface of the intermediate horizontal plate, and a first intermediate column is integrally formed on the upper surface of the intermediate horizontal plate and is brought into contact with the lower surface of the upper horizontal plate.

3. The sensor according to claim 1, wherein a second intermediate column is integrally formed on a lower surface of the intermediate horizontal plate and is brought into contact with an upper surface of the lower horizontal plate, and a first lower column and a second lower column are integrally formed on the upper surface of the lower horizontal plate and are brought into contact with the lower surface of the intermediate horizontal plate.

4. The sensor according to claim 1, wherein a first end portion of the first strain gauge is brought into contact with and assembled with a front surface of an upper column of the upper block, and a second end portion of the first strain gauge is brought into contact with and assembled with a rear surface of a first intermediate column of the intermediate block.

5. The sensor according to claim 4, wherein the upper column and the first intermediate column have the same height as each other and a height of the first strain gauge is less than the height of the upper column and the first intermediate column.

6. The sensor according to claim 1, wherein a first end portion of the second strain gauge is brought into contact with and assembled with a right side surface of a second intermediate column of the intermediate block, and a second end portion of the second strain gauge is brought into contact with and assembled with a left side surface of a first lower column of the lower block.

7. The sensor according to claim 6, wherein the second intermediate column, the first lower column md a second lower column have the same height as one another and a height of the second strain gauge is less than the height of the second intermediate column, the first lower column and the second lower column.

8. The sensor according to claim 1, wherein a signal line wiring hole is formed in the intermediate horizontal plate of the intermediate block so that a signal line of the second strain gauge is configured to pass through the signal line wiring hole.

9. The sensor according to claim 1, wherein a circular support plate is attached on an upper surface of the upper block, and a circular silicon contact plate is attached on the circular support plate.

10. A dummy for measuring a shear force, comprising:
an upper body dummy and a lower body dummy to each of which the sensor for measuring the shear force according to claim 1 is separably mounted; and
a hinge connector connecting the upper body dummy to the lower body dummy using a hinge.

11. The dummy according to claim 10, wherein each of the upper body dummy and the lower body dummy includes a plurality of insertion holes, into each of which the sensor for measuring the shear force is configured to be inserted and fixed, and each of which is formed in a concave shape in a portion thereof making contact with a surface of a vehicle seat.

12. The dummy according to claim 11, wherein a signal line lead-out hole is formed in a portion of an internal wall of each of the insertion holes so that a signal line of the sensor for measuring the shear force is configured to be drawn out through the signal line lead-out hole.

13. The dummy according to claim 11, wherein seventeen or more insertion holes are formed in the upper body dummy at positions corresponding to a spine line thereof, opposite sides of the spine line, and portions thereof making contact with side bolsters of a seatback, and fifteen or more insertion holes are formed in the lower body dummy at positions corresponding to a hip portion thereof, both thigh lines, and portions thereof making contact with side bolsters of a seat cushion.

* * * * *